US009794454B2

(12) United States Patent
Uri et al.

(10) Patent No.: US 9,794,454 B2
(45) Date of Patent: Oct. 17, 2017

(54) CONTACT IMAGER

(71) Applicant: Bio-Rad Laboratories, Inc., Hercules, CA (US)

(72) Inventors: Yochanan Uri, Givat Ela (IL); Boaz Ran, Haifa (IL); Itay Barak, Haifa (IL); Steven Swihart, Walnut Creek, CA (US); Evan Thrush, San Anselmo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 53 days.

(21) Appl. No.: 14/789,717

(22) Filed: Jul. 1, 2015

(65) Prior Publication Data
US 2016/0006910 A1   Jan. 7, 2016

Related U.S. Application Data

(60) Provisional application No. 62/021,517, filed on Jul. 7, 2014.

(51) Int. Cl.
*H04N 5/228* (2006.01)
*H04N 5/225* (2006.01)

(52) U.S. Cl.
CPC .............................. *H04N 5/2252* (2013.01)

(58) Field of Classification Search
CPC ........ H04N 5/225; H04N 5/2252; H04N 5/30; H04N 5/32; H04N 5/3205; H04N 5/321; H04N 5/325; H04N 2201/0412
USPC ...................................................... 348/222.1
See application file for complete search history.

(56) References Cited

U.S. PATENT DOCUMENTS

| | | | | |
|---|---|---|---|---|
| 5,365,564 | A | * | 11/1994 | Yashida ................. A61B 6/505 378/55 |
| 2009/0052616 | A1 | * | 2/2009 | Honjo .................... A61B 6/032 378/19 |
| 2009/0080720 | A1 | * | 3/2009 | Crucs ................... G03B 42/042 382/128 |
| 2014/0103220 | A1 | * | 4/2014 | Ohta .................... A61B 6/4266 250/366 |
| 2014/0308661 | A1 | | 10/2014 | Holmes et al. |
| 2015/0285763 | A1 | * | 10/2015 | Pan ................. G01N 27/44726 204/612 |

FOREIGN PATENT DOCUMENTS

| | | |
|---|---|---|
| JP | 2002049110 A | 2/2002 |
| JP | 2008241447 A | 10/2008 |

OTHER PUBLICATIONS

International Search Report and Written Opinion dated Oct. 6, 2015 in PCT/US15/38856, 12 pages.

\* cited by examiner

*Primary Examiner* — Yogesh Aggarwal
(74) *Attorney, Agent, or Firm* — Kilpatrick Townsend and Stockton LLP

(57) ABSTRACT

Provided herein are imaging cassettes for detecting a luminescent and/or radioactive signals. Such cassettes are useful in common biological assays, e.g., immunoassays, nucleotide detection assays, and other affinity assays.

20 Claims, 8 Drawing Sheets

CONTACT IMAGER

CROSS-REFERENCE TO RELATED PATENT APPLICATIONS

The present application claims benefit of priority to U.S. Provisional Patent Application No. 62/021,517, filed Jul. 7, 2014, which is incorporated by reference for all purposes.

BACKGROUND OF THE INVENTION

Traditionally, results from assays involving luminescent or radioactive labels would be obtained by exposing a blot, membrane, dried gel, etc. to X-ray film. After exposure, the film would be developed so the presence, absence, or intensity of signal from the assay could be determined. Film is convenient for recording results, provides crisp signal, and comparative results. Film results are not, however, quantitative. Moreover, a strong or weak signal can lead to overexposure or underexposure, respectively, so that the exposure must be repeated to obtain useful results. When the assay relies on a chemiluminescent signal that decays with time, it might not be possible to obtain results from a second or third exposure.

Digital imaging, e.g., with a CMOS (complementary metal oxide semiconductor) or CCD (charge coupled device) scanner, allows the user to obtain quantitative results. In some cases however, the result can be distorted or difficult to view, e.g., because of pixel size.

SUMMARY OF THE INVENTION

The present disclosure provides apparatus and techniques that allow results to be obtained simultaneously on film and by digital scanner. This allows the user to obtain the film image for record keeping, while simultaneously learning quantitative information from the digital scan. The digital image can be viewed in real time, and signal strength monitored, so that the film can be developed at an appropriate time. Also provided are apparatus and techniques that allow results to be obtained simultaneously from two opposing digital scanners, which allows for more accurate and sensitive signal detection.

Provided herein are imaging cassettes comprising a base support, an image sensor, and a light tight lid, wherein the imaging cassette is configured to receive a piece of film. For example, when the lid is closed over the base support, a piece of film can be held in place, e.g., by guides in the cassette or by the tightness of the closed lid. In some embodiments, a sample membrane is added to the cassette, e.g., with the sample side facing the sensor or away from the sensor. In some embodiments, a piece of film is added to the cassette, e.g., either above the sample membrane or below.

In some embodiments, the imaging cassette further comprises a transparent cover (e.g., glass or plastic) contacting the image sensor. In some embodiments, the imaging cassette further comprises a fiber plate contacting the image sensor. The transparent cover or fiber plate can protect the image sensor, e.g., from material on the sample membrane or moisture.

In some embodiments, the sample membrane carries a chemiluminescent or radioactive signal or label. In some embodiments, the presence and/or amount of signal indicates the presence and/or amount of a target analyte (e.g., protein or nucleic acid). In some embodiments, the label is indirectly linked to the target analyte through an affinity interaction, e.g., labeled antibody-analyte, labeled antibody-primary antibody-analyte, labeled binding agent-analyte, labeled probe-analyte, etc.

In some embodiments, the image sensor detects wavelengths of 300-800 nm. In some embodiments, the image sensor is a CCD or a CMOS sensor. In some embodiments, the cassette is configured to send signal to a processor (e.g., computer or reader) during or after exposure of the film. In some embodiments, the light-tight lid comprises a second image sensor. The second image sensor can be covered with a transparent cover or fiber plate. In some embodiments, the cassette further comprises a marker, e.g., for identifying or aligning the film and/or digital image, or for creating a signature (e.g., for the date or unique to the user or experiment). The marker can be, e.g., an LED or LCD.

Further provided are dual-sensor devices, e.g., an imaging cassette comprising a base support, an image sensor, and a light-tight lid comprising a second image sensor. In some embodiments, the cassette is configured to receive a sample membrane and/or piece of film. In some embodiments, a sample membrane is added to the cassette. In some embodiments, a piece of film is added to the cassette, e.g., either above the sample membrane or below. Again, the sample membrane can carry a chemiluminescent or radioactive signal or label as described herein.

In some embodiments, the image sensor is covered by a transparent cover or fiber plate. In some embodiments, the second image sensor is covered by a transparent cover or fiber plate. In some embodiments, both image sensors are independently covered by a transparent cover or fiber plate.

In some embodiments, the image sensor detects wavelengths of 300-800 nm. In some embodiments, the image sensor is a CCD or a CMOS sensor. In some embodiments, the cassette is configured to send signal to a processor (e.g., computer or reader) during or after exposure to the sample membrane.

Additionally provided are methods of using the dual-sensor device. In some embodiments, the method comprises placing a sample membrane in the cassette and closing the cassette, thereby generating a digital image from the sample membrane. In some embodiments, the first sensor and the second sensor detect different signals from the sample membrane (e.g., different wavelengths). In some embodiments, the first sensor and second sensor detect the same signals from the sample membrane. In some embodiments, the method further comprises detecting signal from the first and second sensors during or after exposure to the sample membrane. In some embodiments, the method further comprises merging the images generated on the first sensor and second sensor.

Further provided are methods of simultaneously generating a digital image and a film image from a sample membrane comprising:

placing the sample membrane in an imaging cassette comprising a base support, an image sensor, a fiber plate contacting the image sensor, and a light-tight lid;

in a dark environment, placing a piece of film in the cassette; and closing the cassette, wherein, when the lid is closed over the base support, the piece of film is held in place over the fiber plate, thereby simultaneously generating the digital image and film image from the sample membrane. In some embodiments, the imaging cassette is configured to receive a piece of film, and can include, e.g., guides to fit conventional film sizes.

In some embodiments, the method further comprises developing the film and detecting the presence or absence of signal from the sample membrane. In some embodiments, the method further comprises determining from the sensor the presence, absence, or amount of signal from the sample membrane. In some embodiments, the determining is carried out real time while the film is being exposed, i.e., while the piece of film is in the cassette. In some embodiments, the determining is carried out after the film is removed from the cassette. In some embodiments, the sample membrane is placed between the film and the fiber plate. In some embodiments the film is placed between the sample membrane and the fiber plate.

In some embodiments, the image sensor detects wavelengths of 300-800 nm. In some embodiments, the image sensor is a CCD or a CMOS sensor. In some embodiments, the cassette is configured to send signal to a processor (e.g., computer or reader) during or after exposure of the film. In some embodiments, the cassette further comprises a marker, e.g., for identifying or aligning the film and/or digital image. The method can further comprise aligning the image with the signal from the marker (e.g., LED or LCD marker).

DETAILED DESCRIPTION

I. Introduction

Figure 1:
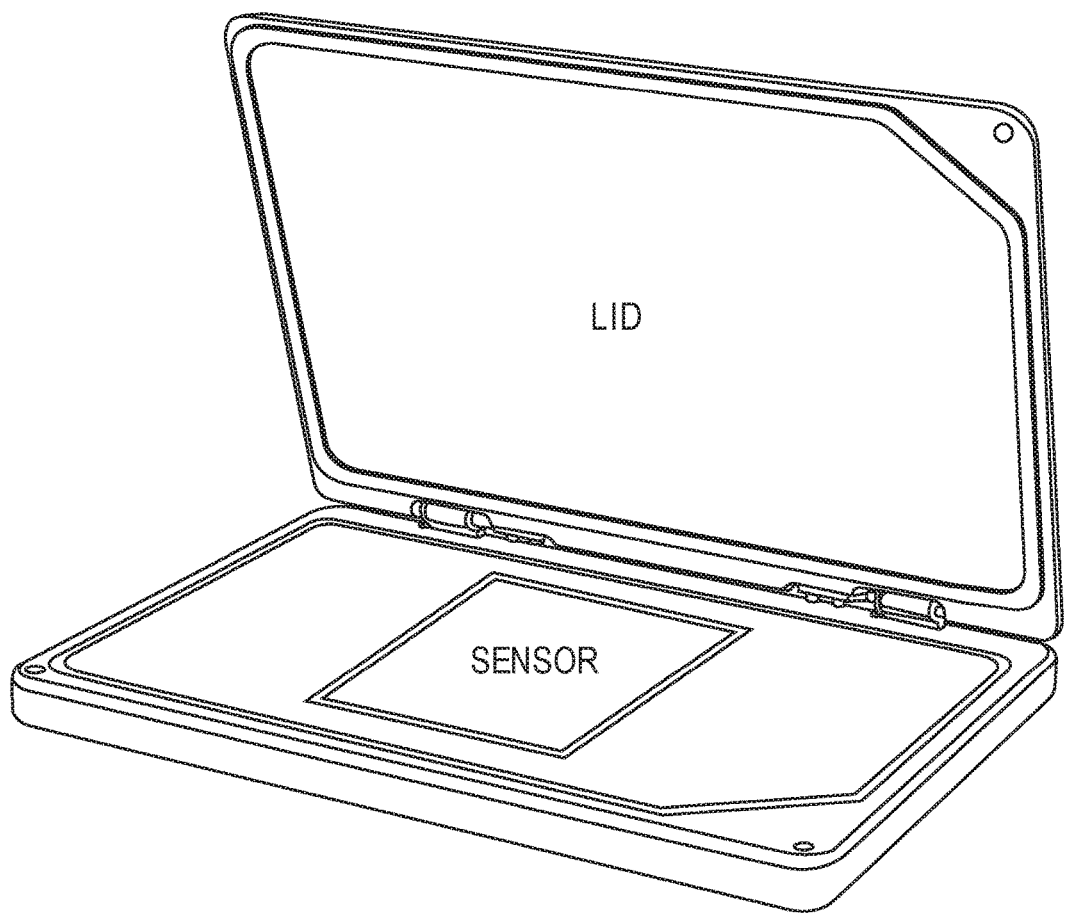
FIG. 1 shows prototype of an imaging cassette embodiment.

Provided herein are devices and methods to obtain a film and digital image simultaneously, or to obtain two digital images simultaneously. This represents the first disclosure of a self-contained "digital film cassette" that allows both film and digital results to be obtained.

The disclosed devices can be used to allow film users to use a digital (contact) imager to enjoy the advantages of both techniques using the same device. The user could digitally monitor the image in real time and know the optimal time to stop exposure of the film. The habitual film user could also test the suitability of a digital scanner and digital results without changing devices, and eventually give up film, again without changing devices.

In some embodiments, the device includes two digital imaging sensors, so that different signals (e.g., radioactive and luminescent, or signals having different wavelengths or intensities) can be obtained simultaneously. Film can optionally be included in the dual-sensor cassette. Three images can thus be captured at the same time, though in some embodiments, the digital images are merged to generate a single image/data set.

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Springs Harbor Press (Cold Springs Harbor, N Y 1989). The following definitions are provided to facilitate understanding of certain terms used frequently herein and are not meant to limit the scope of the present disclosure.

The term "membrane" includes blots and membranes (e.g., nitrocellulose, nylon polyvinylidene fluoride (PDVF), and other materials commonly used in the art). A membrane can also be paper or a paper blend, e.g., where the assay involves transfer of a gel and drying on the paper. A "sample membrane" refers to a membrane carrying sample, e.g., transferred from a gel or applied directly.

The term "sample" or "biological sample" encompasses a variety of sample types obtained from an organism. The term encompasses bodily fluids such as blood, blood components, saliva, serum, plasma, urine and other liquid samples of biological origin, solid tissue biopsy, tissue cultures, or supernatant taken from cultured cells. The biological sample can be processed prior to assay, e.g., to remove cells or cellular debris. The term encompasses samples that have been manipulated after their procurement, such as by treatment with reagents, solubilization, sedimentation, or enrichment for certain components.

As used herein, an "immunoassay" refers to assays that rely on antibody-antigen interactions. Examples include Western blots (antigen transferred to membrane, membrane exposed to antibody, and in some embodiments, secondary antibody); ELISAs; and other affinity-based labeling assays.

The term "antibody" as used herein refers to a polypeptide that specifically binds and recognizes an analyte (antigen). The term encompasses antibodies encoded by an immunoglobulin gene or immunoglobulin genes, recombinant and/or clonal variants thereof, and fragments thereof. A full-length antibody is a tetramer. Each such tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively. The recognized immunoglobulin light chains are classified as either kappa or lambda. Immunoglobulin heavy chains are classified as gamma, mu, alpha, delta, or epsilon, which in turn define the immunoglobulin classes, IgG, IgM, IgA, IgD and IgE, respectively.

Antibodies exist as intact immunoglobulins or as well-characterized antigen-binding fragments produced by digestion of intact immunoglobulins with various peptidases. Thus, for example, pepsin digests an antibody near the disulfide linkages in the hinge region to produce F(ab')2, a dimer of Fab which itself is a light chain joined to VH-CH1 by a disulfide bond. The F(ab')2 dimer can be reduced under mild conditions to break the disulfide linkage in the hinge region, thereby converting the F(ab')2 dimer into two Fab' monomers. The Fab' monomer is essentially an Fab with part of the hinge region (see, Paul (Ed.), Fundamental Immunology, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or by de novo synthesis using recombinant DNA methodologies such as single chain Fv.

Antibodies are commonly referred to according their targets. While the nomenclature varies, one of skill in the art will be familiar and understand that several names can be applied to the same antibody. For example, an antibody specific for PSA can be called "anti-PSA," "PSA antibody," "anti-PSA antibody," etc.

The terms "antigen," "immunogen," "antibody target," "target analyte," and like terms are used herein to refer to a molecule, compound, or complex that is recognized by an antibody, i.e., can be specifically bound by the antibody. The term can refer to any molecule that can be specifically recognized by an antibody, e.g., a polypeptide, polynucleotide, carbohydrate, lipid, chemical moiety, or combinations thereof (e.g., phosphorylated or glycosylated polypeptides, etc.).

The terms "specific for," "specifically binds," and like terms refer to a molecule (e.g., antibody or antibody fragment) that binds to its target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a given antibody target will typically bind the antibody target with at least a 2-fold greater affinity than a non-antibody target. Specificity can be determined using standard methods, e.g., solid-phase ELISA immunoassays (see, e.g., Harlow & Lane, Using Antibodies, A Laboratory Manual (1998) for a description of immunoassay formats and conditions that can be used to determine specific immunoreactivity).

The term "binds" with respect to an antibody target (e.g., antigen, analyte), typically indicates that an antibody binds a majority of the antibody targets in a pure population (assuming appropriate molar ratios). For example, an antibody that binds a given antibody target typically binds to at least ⅔ of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

The terms "label," "detectable label, "detectable moiety," and like terms refer to a composition detectable by spectroscopic, photochemical, biochemical, immunochemical, chemical, or other physical means. In the context of the present disclosure, labels typically include, luminescent agents, electron-dense reagents, enzymes (e.g., as commonly used in an ELISA), biotin, digoxigenin, $^{32}P$ and other isotopes, haptens, and proteins which can be made detectable, e.g., by incorporating a radiolabel into the peptide or used to detect antibodies specifically reactive with the peptide. The term includes combinations of single labeling agents, e.g., a combination of dyes that provides a unique detectable signature, e.g., at a particular wavelength or combination of wavelengths. Any method known in the art for conjugating label to a desired agent may be employed, e.g., using methods described in Hermanson, Bioconjugate Techniques 1996, Academic Press, Inc., San Diego.

The term "positive," when referring to a result or signal, indicates the presence of an analyte or item that is being detected in a sample. The term "negative," when referring to a result or signal, indicates the absence of an analyte or item that is being detected in a sample. Positive and negative are typically determined by comparison to at least one control, e.g., a threshold level that is required for a sample to be determined positive, or a negative control (e.g., a known blank).

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters, and will understand which controls are valuable in a given situation and be able to analyze data based on comparisons to control values. Controls are also valuable for determining the significance of data. For example, if values for a given parameter are variable in controls, variation in test samples will not be considered as significant.

III. Imaging Cassettes

The presently disclosed devices have an outer shell including the base plate and light-tight lid that is made out of a durable material (e.g., plastic, metal, alloy, etc.). The outer shell acts to protect the sensor (e.g., from moisture), provide mechanical support, and prevent disruption of the exposure. The sensor can be thermally bonded or coupled to a slab (e.g., aluminum or other alloy) that provides mechanical support and reduces temperature gradients across the sensor. The lid can clasp onto the base plate or otherwise close securely to ensure that light does not enter during exposure of the sensor and/or film to signal on a sample membrane.

The base plate and lid are configured to receive a piece of film and/or sample membrane into the cassette. The base plate and lid can also act to hold the film and/or sample membrane in place during exposure to avoid blurring of the film or digital image. This can be accomplished by ensuring that the lid closes tightly enough over the base plate and fiber plate (if present) so that the film and/or sample membrane do not move. The cassette can also include guides, e.g., inside the base plate or on the lid to hold the film and/or sample membrane (e.g., in conventional sizes such as 5"×7", 8"×10", or 10"×12"). The inside surface of the light-tight lid can include a flexible or semi-rigid material, e.g., rubber or foam padding, or a spring-loaded pad, to allow for some flexibility in the thickness of the film and/or sample membrane. The outer border of the base plate and/or light-tight lid can also include a flexible or semi-rigid material (e.g., a rubber border) to ensure tight fit.

The base plate holds an imaging sensor as described herein, with a transparent cover, fiber plate, or gradient index (GRIN) lens array covering the sensor for protection and transmission of signal from the sample membrane to the sensor. The base plate also is configured to transmit a signal (e.g., data that comprise the digital image of signals from the sample membrane) to an external device (e.g., processor, scanner, computer) during or after exposure of the sample membrane in the cassette. A control board coupled to the sensor is used to transmit the signal from the sensor, and communicate it to an external device, optionally with a user interface. The external device can be a touch screen (e.g., integrated in the lid or separate), hand-held device (e.g., tablet or smartphone), or other processor or computer. Communication can be via cables or ports (e.g., USB or Ethernet) on the cassette, or wirelessly (e.g., using Bluetooth or other wireless transmission). In dual-sensor devices, the light-tight lid also holds an imaging sensor with a fiber plate covering it. When there is no membrane or film in the dual-sensor cassette, the fiber plates are in contact or nearly in contact with the sensors on either side (see FIGS. 5-7).

The presently described devices can be provided in any convenient size. Typical Western blots, dot blots, Northern blots, and Southern blots are on the order of a few inches on either side (e.g., 2×3, 3×4, 4×8 inches), so that a relatively small cassette and sensor detection area will suffice for most assays, e.g., in the range of about 10×12 inches. Sequencing gels are typically larger, thus a cassette having larger dimensions, e.g., in the range of 20×36 inches, can be provided.

IV. Assays and Materials

The presently disclosed devices are best suited for assays relying on chemiluminescent, bioluminescent, or radioactive signals. Such assays include Western blots, ELISAs, immunoassays, Northern blots (e.g., expression studies using a reporter gene), Southern blots, nucleic acid sequencing assays, assays involving viral or bacterial labeling (e.g., CFU or expression studies). Assay protocols can be found in, e.g., Walker (2009 $3^{rd}$ ed.) Protein Protocols Handbook; Hilario, Protocols for Nucleic Acid Analysis by Nonradioactive Probes (2007 $2^{nd}$ ed.); Wenk, A Manual for Biochemistry Protocols (2007); Harris, Cell Biology Protocols (2006); etc.

Common chemiluminescent substrates and labels include aequorin, NADP, luciferin phosphate, umbelliferyl phosphate, p-nitrophenyl phosphate Enzymes used in such assays include horseradish peroxidase (HRP), luciferase (e.g., firefly luciferase), alkaline phosphatase, β-D-galactosidase, glucose-6-phosphate dehydrogenase, xanthine oxidase (see, e.g., Krick (1991) *Clin Chem* 37:1472 for background).

Applicable assays include those involving a radioisotope label, e.g., radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga.

In some embodiments, the assay involves transferring sample that potentially includes a target analyte (e.g., protein, DNA, RNA) to a membrane (e.g., blot); exposing the membrane to a first binding reagent that specifically binds to the target analyte (e.g., labeled probe or antibody). The sample can be on a gel (e.g., electrophoretic gel such as PAGE or agarose gel) or a culture dish before transfer, or can be directly applied to the membrane by the user. In some embodiments, the assay further involves exposing the membrane to a second binding reagent that specifically binds the first binding reagent (e.g., a labeled secondary antibody, or labeled affinity agent such as streptavidin (to bind biotin on the first binding reagent)). Such assays typically involve washes between binding steps.

In some embodiments, sample is applied directly to the membrane, e.g., pipetted onto the membrane. This can be useful for controls, e.g., dilution series with known amounts of analyte, or positioning signals.

A membrane carrying sample (e.g., after transfer of the protein, nucleic acid, or other sample from a gel to the membrane) can be exposed to an index matching fluid. The index matching fluid increases the transparency of the membrane, and/or matches it to the refractive index of the fiber or sensor, thereby reducing any potential interference of the membrane with signal. The fluid closely approximates that of the sensor or fiber to reduce reflection at the surface of the interface. Examples of index matching fluids are fused silica matching fluids from Cargille.

V. Sensors

The sensor component(s) of the cassette can be any complementary metal oxide semiconductor (CMOS) or charge coupled device (CCD). Such sensors and methods of use are familiar in the art, e.g., Fraden (Springer, $4^{th}$ ed.) Handbook of Modern Sensors: Physics, Designs, and Applications; Cabello et al. (2007) *Phys Med Biol* 52:4993. Useful sensors are available from a number of commercial suppliers, e.g., Cannon, Samsung, Toshiba, CMOS Sensor, etc.

Both CCD and CMOS devices have a 2-D array of thousands or millions of tiny cells, each of which transforms the signal (light of radiation) from one small portion of the image into electrons. Once an image is captured on the sensor, the next step is to read the value (accumulated charge) of each cell in the image. In a CCD device, the charge is actually transported across the chip and read at one corner of the array. An analog-to-digital converter turns each pixel's value into a digital value. In most CMOS devices, there are several transistors at each pixel that amplify and move the charge using more traditional wires. The CMOS approach is more flexible because each pixel can be read individually. CCDs use a special manufacturing process to create the ability to transport charge across the chip without distortion. This process leads to very high-quality sensors in terms of fidelity and light sensitivity.

Current CCD and CMOS imaging systems are limited to producing a digital image, e.g., the C-DiGit Blot Scanner, Dexela, or myECL Imager. Similar imaging technology and software can be employed in the presently described cassettes. The present cassettes however, are separate, portable devices that are convenient to use. The cassette can be linked to a computer or scanner during or after exposure to detect the presence, absence, and/or strength of signal.

Acquisition of signal from the sensor can be accomplished by a control board, e.g., placed inside the base plate below the sensor, or externally. The sensor can thus be connected to the board with a cable or if external, via a port or wireless connection. The control board can then communicate with an external device that can provide a user interface. The external device can be a touch screen (e.g., attached to the lid or separate), hand-held device (e.g. smartphone or tablet), or other processor, computer, or storage device. The external device can be accessed by cables or ports on the cassette (e.g., USB or Ethernet) or by wireless signals (e.g., WiFi or Bluetooth).

In some embodiments, the sensor is covered by a transparent cover, e.g., glass or plastic, that is a non-fiber material. In some embodiments, the sensor is covered by a fiber plate (or Fiber Optic Plate (FOP)) that transmits signal from the sample membrane to the sensor. The fiber plate includes a bundle of single fibers that conveys light (or radiation) and an absorber glass that absorbs light leaking from each fiber. The fiber plate directly conveys signal from the input surface (membrane) to the output surface (sensor) without degradation from signal leaking from adjacent fibers within the plate. Fiber plates are commercially available, e.g., from INCOM and Proxivision. Materials for the transparent cover or fiber plate include glass (e.g., low melting point glasses, such as borosilicates, or other lead-based glasses), polycarbonate, polystyrene, or other transparent polymers. The transparent cover or fiber plate can also be coated, e.g., with a protective shield or non-reflective coating. In some embodiments, the sensor is covered by a gradient index (GRIN) lens array. The GRIN lens array has two flat and parallel surfaces and the focusing action is obtained by a variation of refractive index across the lens (see, e.g., Ye & McLeod (2008) *Optics Letters* 33:2575).

In some embodiments, the cassette can be cooled during exposure. Cooler temperatures reduce dark current (potential noise source for the digital image), and enable longer exposure times which can increase sensitivity. Cooling does, however, slow the chemical reaction in the case of chemiluminescent signal. The user can determine whether to cool the cassette depending on desired speed and sensitivity considerations.

In some embodiments, the cassette includes a marker, e.g., an LED (light emitting diode), LCD (liquid crystal diode), or small illuminated display, for marking or aligning the film. For example, a small LED or back illuminated LCD can be placed in a corner of the lid, baseplate, or fiber plate to mark the designated position on the film and/or image. The LED or LCD can be turned on for a short period so as to avoid saturating the film (e.g., 0.1-2 seconds, depending on the comparative strength of the signal from the sample). The strength of the LED or LCD signal can be adjusted on the digital image, e.g., using a non-destructive readout (NDR) imager. In some embodiments, the LED or LCD is configured into a signature, e.g., user initials, date, etc., and can be replaced or programmed appropriately. For example, the LCD can have back illumination to allow the signal to be shaped into a signature, character, or symbol by programing the crystal device to allow light through in a certain pattern. The LED can comprise a dot array, or be included in an array of LEDs.

VI. Examples

Provided herein are two imaging device concepts. In the first, film and a digital image from a sensor are simultaneously generated. In the second, the device carries two sensors, and can optionally be used to generate a film image as well.

An embodiment of the first concept is shown in FIG. 1. The ability to generate both a film and digital image can ease transition to digital imaging. The images are generated at the same time with a single, portable instrument. This prevents the need to scan the film later for record keeping. In addition, a digital image allows for quantification of signal without having to give up the film image. Conveniently, the sensor can be monitored in real time, while the film is exposing, so the user can monitor film exposure in real time and know the optimal time to stop the exposure.

The second concept can be used to increase absolute sensitivity (e.g., for detection of a scarce sample or weak signal), to reduce time to result (e.g., to detect signal above background or signal of a desired strength). Film can also be used with the dual-sensor device. In such cases, the sensor closest to the film could be disabled, or could be active, e.g., with sharpening algorithms applied if necessary to correct for any potential interference from the film.

Example 1

Configurations for Use of Single-Sensor Device

Figure 2:
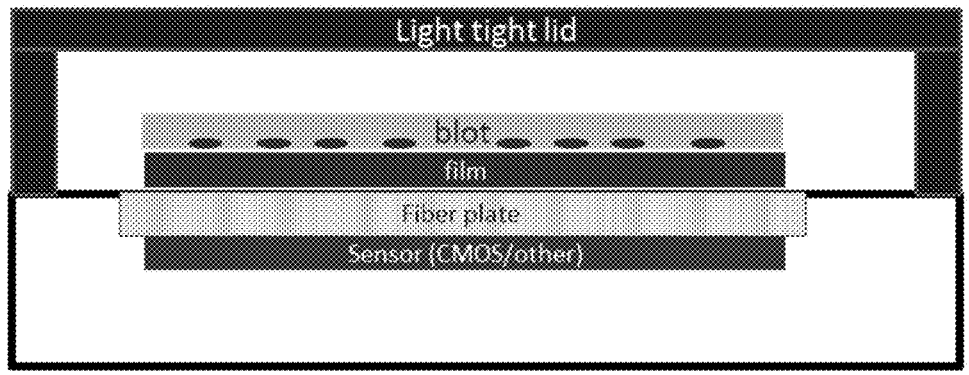
FIG. 2 shows a side, cutaway view of an imaging cassette embodiment. In this embodiment, film rests directly on the fiber plate, and the membrane (blot) is placed on top of the film, with the sample side facing downward. Signal (e.g., light) emitted from the labeled sample (e.g., protein bands or spots) on the membrane passes through the film and is then detected by the image sensor.
Figure 3:
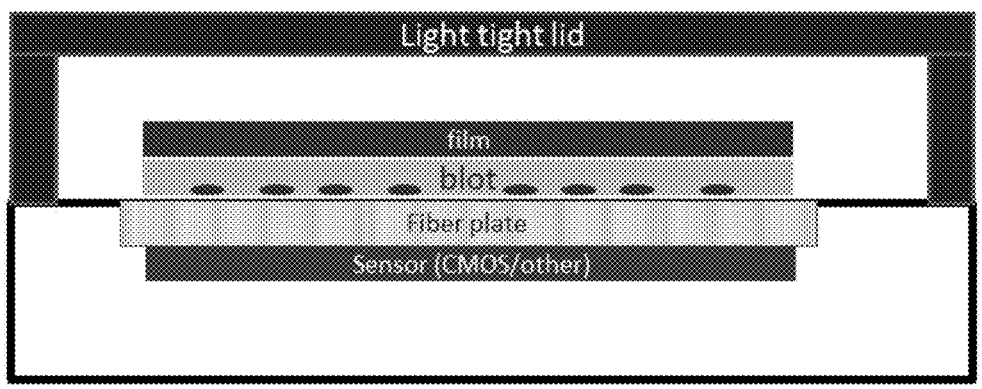
FIG. 3 shows a side, cutaway view of an imaging cassette embodiment. In this embodiment, the membrane (blot) is placed directly on top of the fiber plate, sample side facing downward. Film is placed on top of the membrane. Both film and sensor detect signal from the labeled sample on the membrane. If the membrane interferes with signal, this embodiment will provide a higher quality digital image.
Figure 4:
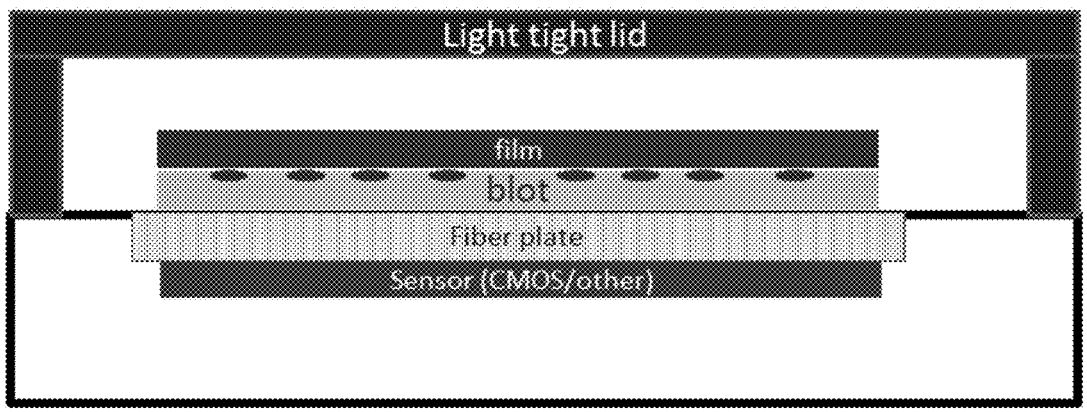
FIG. 4 is similar to the view shown in FIG. 3, but the sample side of the membrane faces up. If the membrane interferes with signal, this embodiment will provide a higher quality film image.

Examples of how the single-sensor device can be used are shown in FIGS. 2-4.

Both the film and the blot membrane are placed one on top the other inside the imaging cassette. The film can be placed below the blot (relative to the sensor) or above, as shown in FIGS. 2 and 3, respectively.

If the film is placed between the sensor and the blot (FIG. 2), light emitted from the bands on the blot has to pass through the film before it reaches the fiber face plate. While the light travels through the thickness of the film it can scatter slightly (depending on film thickness) leading to some degree of loss in image quality of the digital image (e.g., resolution), but obtaining maximum quality on the film image. This can be corrected with sharpening algorithms for the digital image.

If the blot is placed directly on the fiber plate with the sample side facing down (FIG. 3), the digital image would achieve maximal quality while the film image might be compromised, depending on optical density of the blot membrane. The blot can also be placed on the fiber plate with the sample side facing up towards the film as in FIG. 4. In this configuration, signal emitted from the bands will enter directly into the film without having to pass through the thickness of the blot, while light traveling downward towards the sensor will need to pass through the blot. As shown in Example 3, interference from the membrane does not raise a major issue. If interference from the membrane is detected, the membrane can be contacted with an index matching fluid before it is placed in the cassette.

Example 2

Configurations for Use of Dual-Sensor Device

Figure 5:
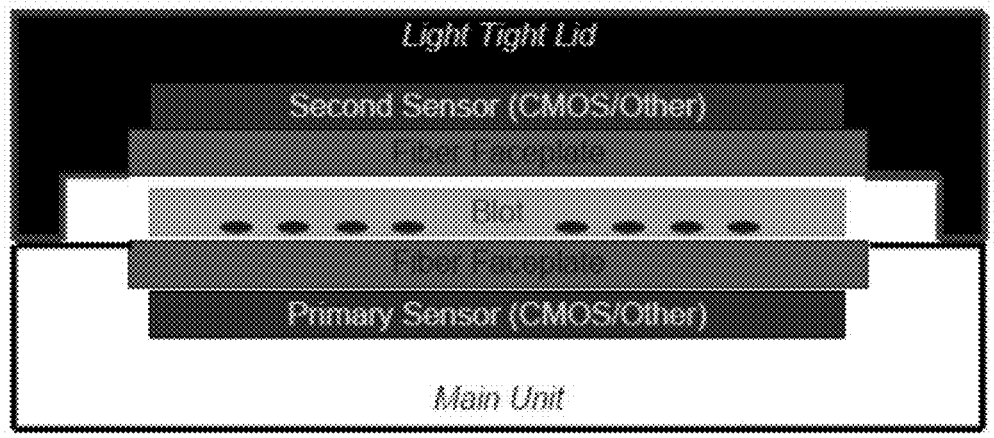
FIG. 5 shows a side, cutaway view of a dual-sensor imaging cassette embodiment. The membrane rests directly on the fiber plate above the first sensor in the main unit, and the lid holding the second sensor and fiber plate is closed over the membrane. Signal emitted from the labeled sample on the membrane is detected by both sensors.
Figure 6:
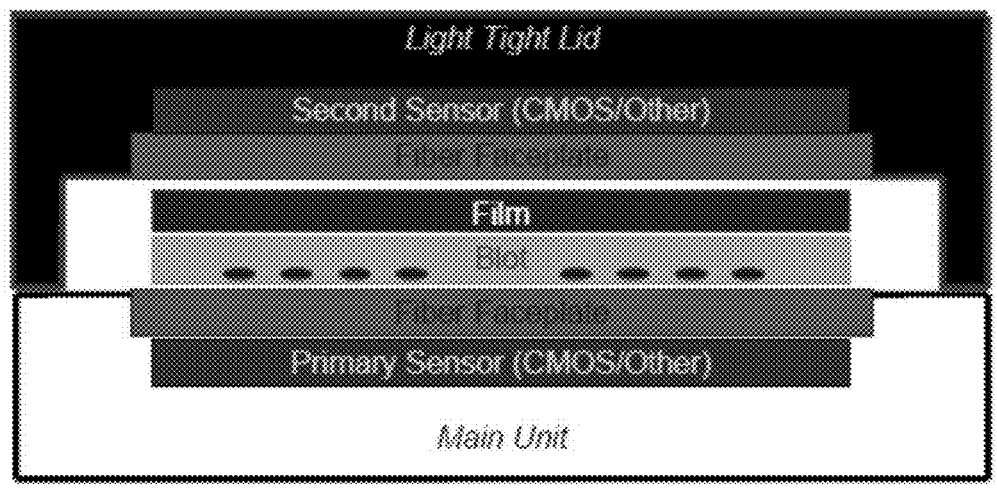
FIG. 6 shows a side, cutaway view of a dual-sensor imaging cassette embodiment, this time with film inserted above the membrane on the bottom fiber plate. Signal emitted from the labeled sample on the membrane passes through the film, and is detected by both sensors.
Figure 7:
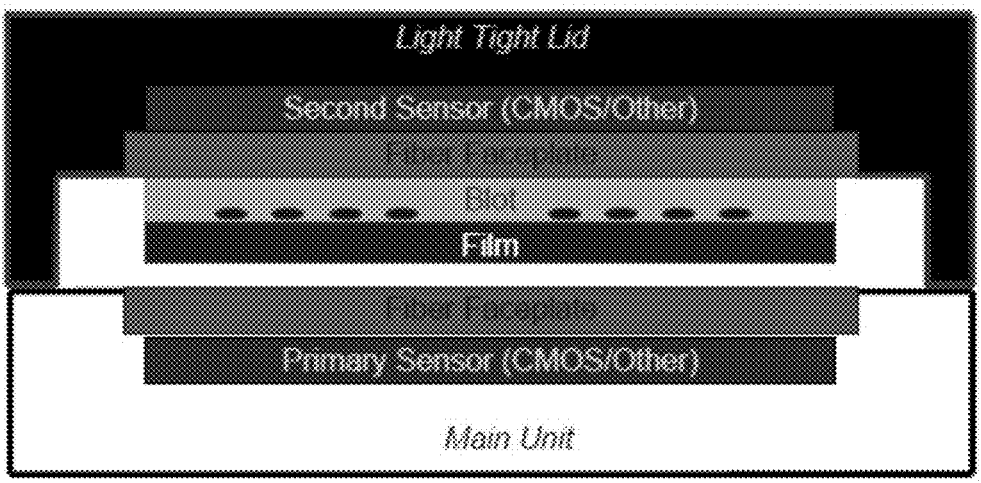
FIG. 7 is similar to the view shown in FIG. 6, but with the film and membrane reversed.

Examples of how the dual-sensor device can be used are shown in FIGS. 5-7.

FIG. 5 shows the blot sample side down on the fiber plate of the primary sensor and closed lid carrying the second sensor and fiber plate. Film can also be included with the dual-sensor device, as shown in FIGS. 6 and 7.

Example 3

Effect of Sample Membrane Placement on Signal

Figure 8:
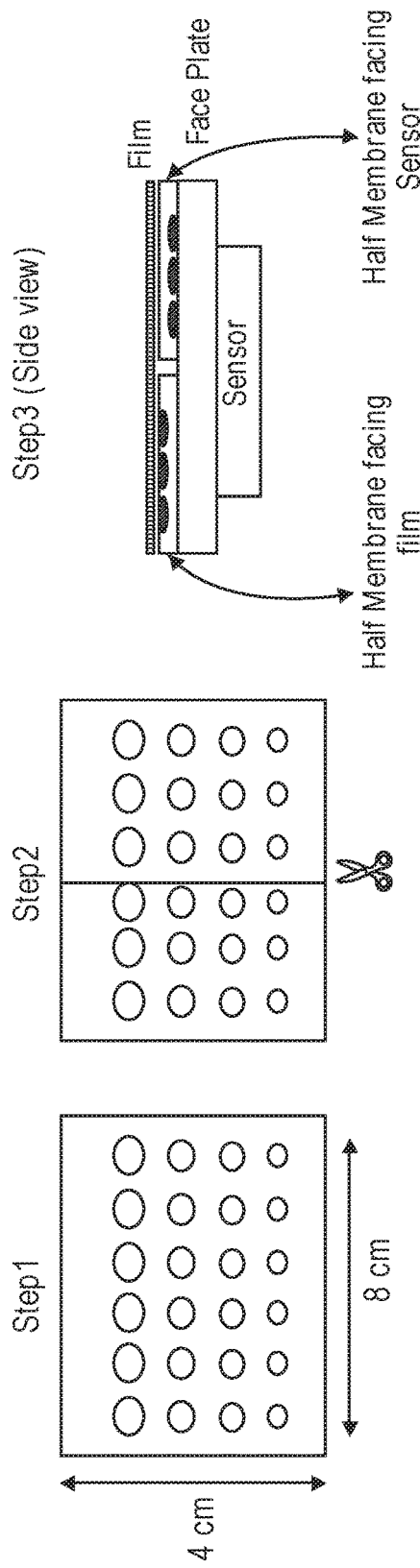
FIG. 8 outlines a test of whether membrane interferes with signal, the results of which are shown in FIGS. 9-11 for various substrates.

A potential complication is interference of a membrane with signal, where the labeled analyte is on one side of the membrane and the sensor and/or film is on the other (non-analyte) side of the membrane. To determine if this would be an issue, we prepared a single membrane (8 cm×4 cm) and blotted with a dilution series, as shown in FIG. 8. The membrane was cut into identical halves, one placed in an imaging cassette with labeled analyte (sample) side up facing the film, the other placed in the imaging cassette with labeled analyte side down facing the fiber plate and sensor.

Figure 9:
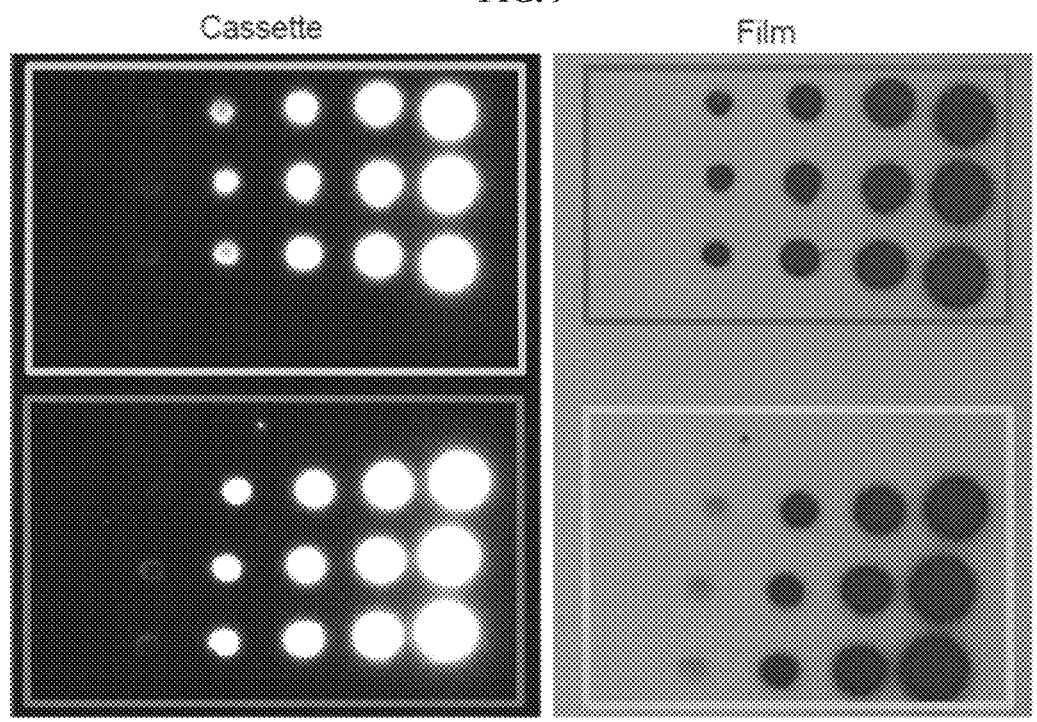
FIG. 9 shows results using Westar® Supernova substrate. The top panel shows a 1 minute exposure of a dilution series with 200, 66, 22, 7, 2.5, and 0.8 pg. The lower panels compare results of the 1 minute exposure to those with longer exposure times.
Figure 9:
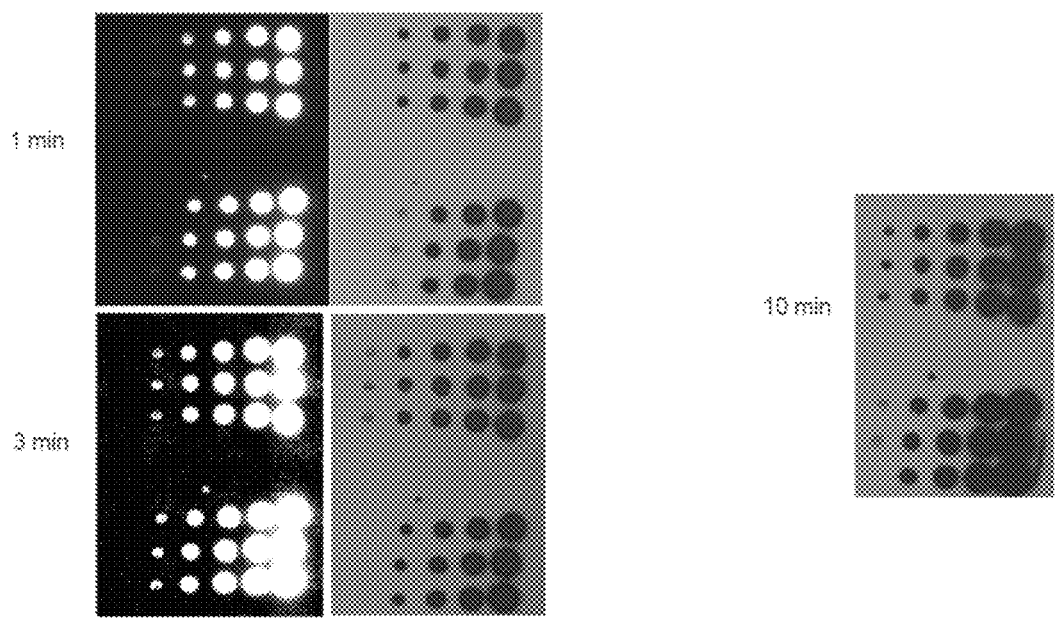
Figure 10:
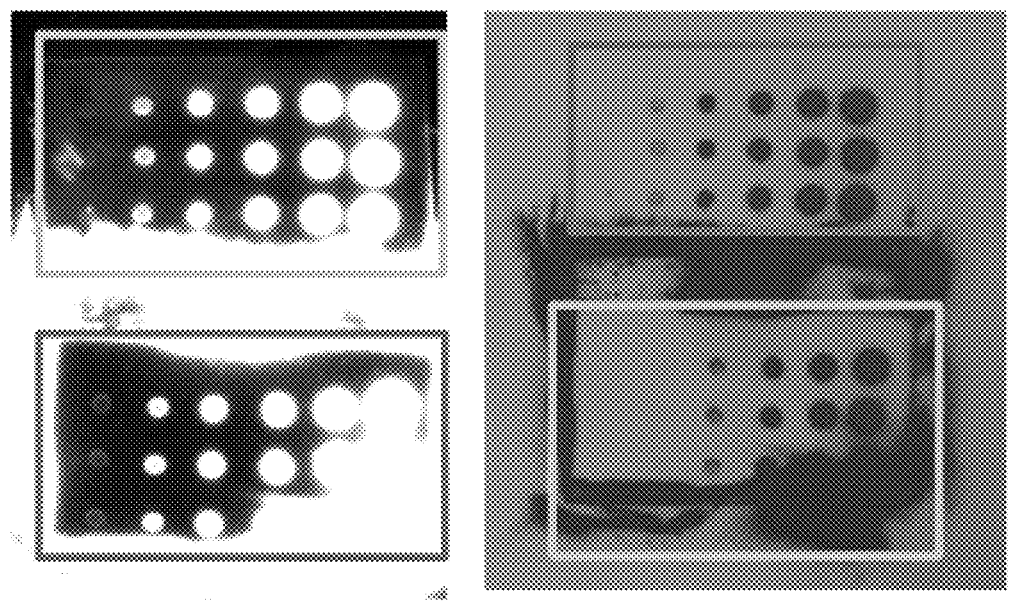
FIG. 10 shows results using Supersignal® West Femto substrate (Thermo). The top panel shows a 1 minute exposure of a dilution series with 200, 66, 22, 7, 2.5, and 0.8 pg. The lower panels compare results of the 1 minute exposure to those with longer exposure times.
Figure 10:
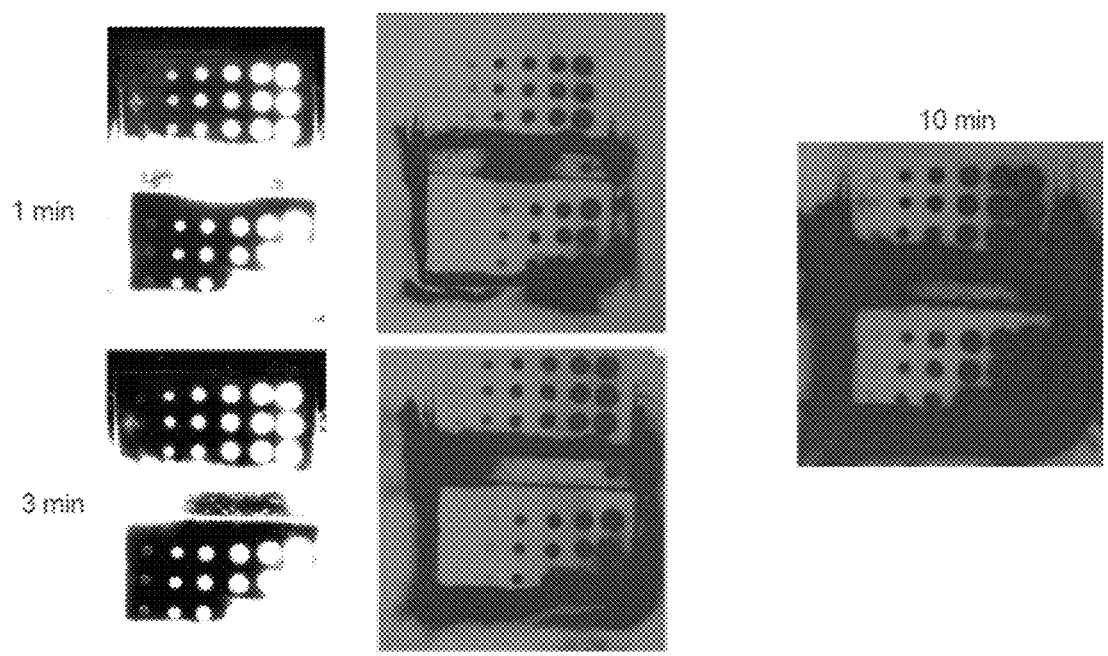
Figure 11:
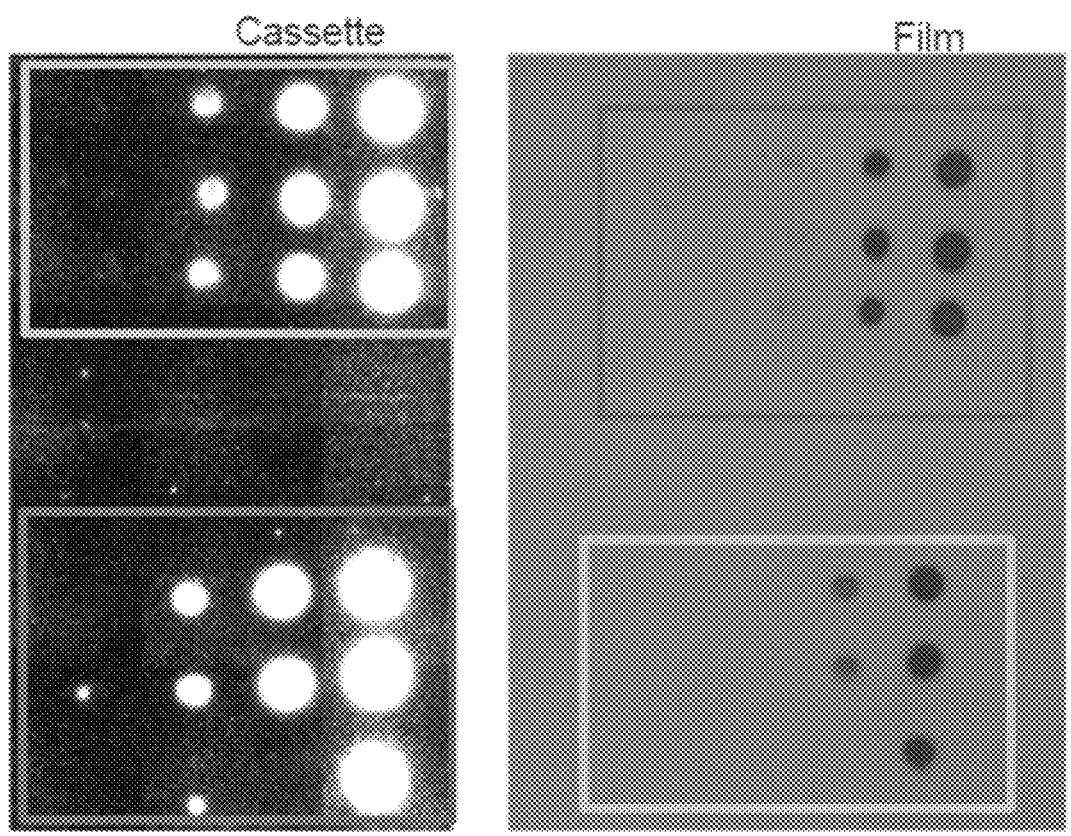
FIGS. 11 A and 11 B show results using Clarity™ substrate (Bio-Rad). The first panel shows a 1 minute exposure of a dilution series with 200, 100, 50, 25, 22.5, and 11.25 pg. The next panels compare results of the 1 minute exposure to those with longer exposure times.
Figure 11B:
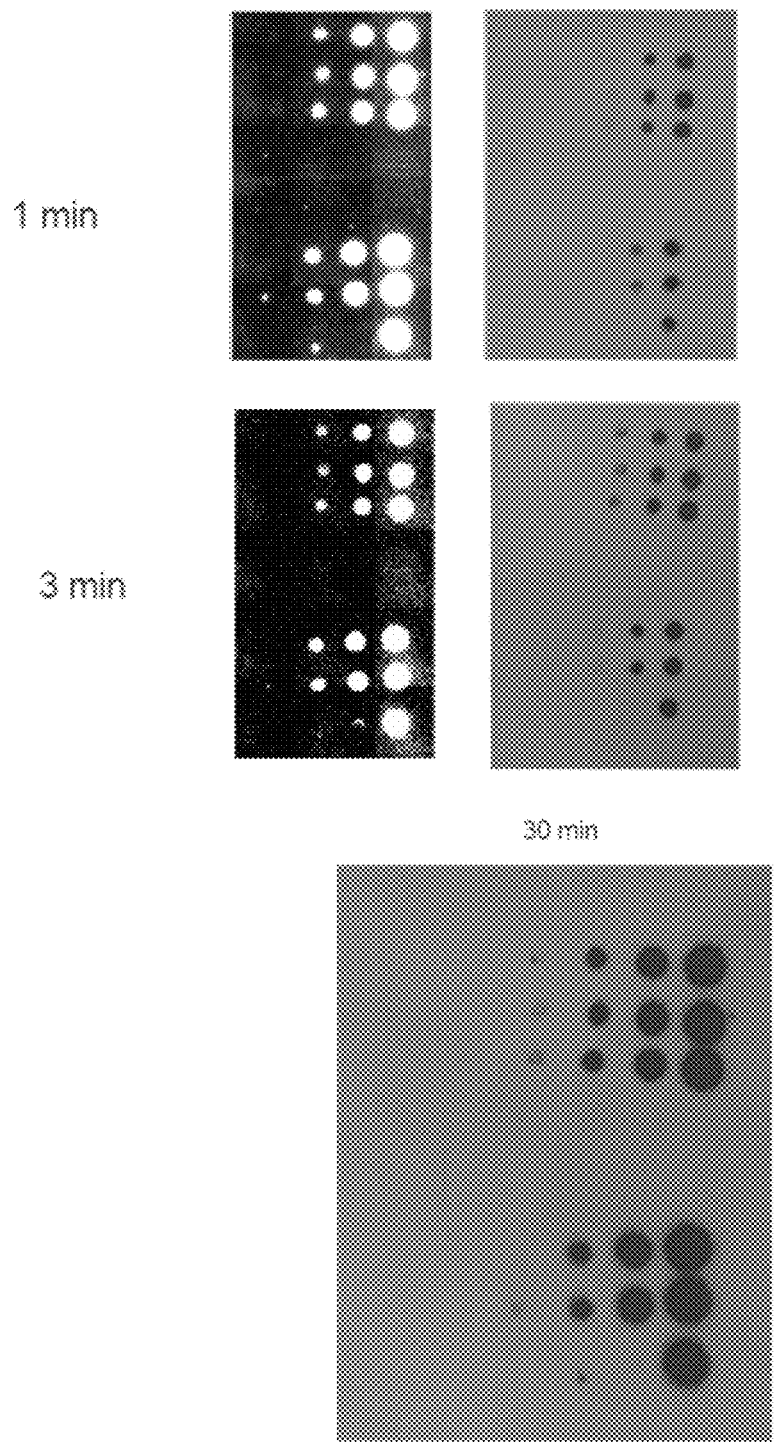

The membrane was developed using three different substrates: Westar® Supernova, Supersignal® West Femto, and Clarity™ substrates. The results are shown, respectively, in FIGS. 9-11.

The results show that the orientation of the membrane (sample-side up or down) has little effect on either digital or film images, especially at the higher concentrations.

At the lower end of detection, a slight difference is detectable. For example, in FIG. 9, a slight difference can be detected in the fourth dilution (7 pg) with the Supernova substrate. The fourth row of spots is lighter in the top left image (representing the membrane sample side facing away from the sensor), than the fourth row of spots in the bottom left image (representing the membrane sample side facing toward the sensor). Similarly, the fourth row of spots is darker in the top right image (representing the membrane sample side facing toward the film), than the fourth row of spots in the bottom right image (representing the membrane sample side facing away from the film).

Generally, however, the membrane does not significantly interfere with detection of signal in any of the substrate systems we tested. In cases where optimal signal quality is desired for both film and the digital image, the membrane can be placed between the fiber plate and the film, with the sample side facing either direction (see, e.g., FIG. 3 or 4).

It is understood that the examples and embodiments described herein are for illustrative purposes only and that various modifications or changes in light thereof will be suggested to persons skilled in the art and are to be included within the spirit and purview of this application and scope of the appended claims. All patents, patent applications, internet sources, database entries, and other published materials cited in this specification are incorporated herein by reference in their entireties. Any discrepancy between any reference material cited herein or any prior art in general and an explicit teaching of this specification is intended to be resolved in favor of the teaching in this specification.

What is claimed is:

1. An imaging cassette comprising a base support, an image sensor, and a light-tight lid, wherein the imaging cassette is configured to receive a piece of X-ray film and sample membrane when the image sensor is present in the imaging cassette, wherein the imaging cassette is configured to receive the sample membrane between the X-ray film and the image sensor or wherein the imaging cassette is configured to receive the sample membrane between the X-ray film and the light-tight lid.

2. The imaging cassette of claim 1, further comprising a fiber plate or a transparent cover contacting the image sensor.

3. The imaging cassette of claim 1, further comprising a sample membrane.

4. The imaging cassette of claim 1, further comprising a piece of film.

5. The imaging cassette of claim 3, wherein the sample membrane carries a chemiluminescent or radioactive label.

6. The imaging cassette of claim 4, wherein the sample membrane is placed between the film and the image sensor.

7. The imaging cassette of claim 4, wherein the film is placed between the sample membrane and the image sensor.

8. The imaging cassette of claim 1, wherein the image sensor detects wavelengths of 300-800 nm.

9. The imaging cassette of claim 1, further comprising an LED or LCD marker.

10. The imaging cassette of claim 1, wherein the light-tight lid comprises a second image sensor.

11. An imaging cassette comprising a base support, an image sensor, and a light-tight lid comprising a second image sensor, wherein the light-tight lid can be opened and closed to receive a sample membrane and/or piece of film.

12. The imaging cassette of claim 11, further comprising a fiber plate or transparent cover contacting the image sensor, the second image sensor, or both.

13. The imaging cassette of claim 11, further comprising a sample membrane.

14. The imaging cassette of claim 11, further comprising a piece of X-ray film.

15. The imaging cassette of claim 11, wherein the sample membrane carries a chemiluminescent or radioactive label.

16. The imaging cassette of claim 11, wherein the image sensor detects wavelengths of 300-800 nm.

17. A method of simultaneously generating a digital image and a film image from a sample membrane comprising:
  placing the sample membrane in an imaging cassette comprising a base support, an image sensor, and a light-tight lid;
  in a dark environment, placing a piece of film in the cassette;
  closing the cassette, wherein, when the lid is closed over the base support, the piece of film is held in place over the fiber plate, and
  thereby simultaneously generating the digital image and film image from the sample membrane.

18. The method of claim 17, wherein the imaging cassette further comprises a fiber plate or transparent cover contacting the image sensor.

19. The method of claim 17, further comprising developing the film and detecting the presence or absence of signal from the sample membrane.

20. The method of claim 17, further comprising determining from the sensor the presence, absence, or amount of signal from the sample membrane.

* * * * *